United States Patent
Van Haag et al.

(10) Patent No.: US 9,568,424 B2
(45) Date of Patent: Feb. 14, 2017

(54) CARTRIDGE, SYSTEM AND METHOD FOR AUTOMATED MEDICAL DIAGNOSTICS

(75) Inventors: Chris Van Haag, Eindhoven (NL); Michiel Johannes Jongerius, Eindhoven (NL); Danny Genius Aldegonda Schaefer, Eindhoven (NL); Adrianus Wilhelmus Dionisius Maria Van Den Bijgaart, Eindhoven (NL); Ronald De Gier, Eindhoven (NL); Michiel De Jong, Eindhoven (NL); Gerhard Pross, Weil Im Schoenbuch (DE); Johannes Bacher, Leonberg (DE); Andreas Boos, Bondorf (DE); Gerd Luedke, Holzgerlingen (DE); Jens-Peter Seher, Stuttgart (DE)

(73) Assignee: BIOCARTIS NV, Mechelen (BE)

( * ) Notice: Subject to any disclaimer, the term of this patent is extended or adjusted under 35 U.S.C. 154(b) by 736 days.

(21) Appl. No.: 11/917,955

(22) PCT Filed: Jun. 16, 2006

(86) PCT No.: PCT/IB2006/051941
§ 371 (c)(1),
(2), (4) Date: Dec. 18, 2007

(87) PCT Pub. No.: WO2006/136990
PCT Pub. Date: Dec. 28, 2006

(65) Prior Publication Data
US 2010/0047774 A1    Feb. 25, 2010

(30) Foreign Application Priority Data
Jun. 23, 2005 (EP) .................................. 05105608

(51) Int. Cl.
*C12M 1/36* (2006.01)
*G01N 21/64* (2006.01)
(Continued)

(52) U.S. Cl.
CPC ..... *G01N 21/6428* (2013.01); *B01L 3/502715* (2013.01); *B01L 3/545* (2013.01);
(Continued)

(58) Field of Classification Search
USPC ................................. 435/287.1, 6
See application file for complete search history.

(56) References Cited

U.S. PATENT DOCUMENTS

| | | |
|---|---|---|
| D37,164 S | 10/1904 | Hilbom |
| 4,479,760 A | 10/1984 | Bilstad et al. |

(Continued)

FOREIGN PATENT DOCUMENTS

| | | |
|---|---|---|
| EP | 1418243 A2 | 5/2004 |
| EP | 1430948 A1 | 6/2004 |

(Continued)

OTHER PUBLICATIONS

Choi et al., A Disposable Plastic Biochip Cartridge with On-chip Power Sources for Blood Analysis, Proceedings of the IEEE 16th Annual International Conference on Micro Electro Mechanical Systems. MEMS 2003, Kyoto, Japan, pp. 19-23; [IEEE International Micro Electro Mechanical Systems Conference], New York, NY: IEEE, US, vol. Conf. 16, XP010637005, DOI: 10.1109/MEMSYS.2003.1189782, ISBN: 978-0-7803-7744-8, pp. 447-450 (Jan. 19, 2003).

(Continued)

*Primary Examiner* — Betty Forman
(74) *Attorney, Agent, or Firm* — Greenblum & Bernstein, P.L.C.

(57) ABSTRACT

Cartridge and method for the detection of the presence, absence and/or amount of a target nucleotide sequence in a sample comprising one or more nucleic acid sequences. The cartridge comprises a one or more nucleic acid sequences, and the cartridge includes a generic part and one or more (Continued)

separate application-specific parts, which are connectable to the generic part.

16 Claims, 5 Drawing Sheets

(51) Int. Cl.
  *B01L 3/00* (2006.01)
  *G01N 35/00* (2006.01)

(52) U.S. Cl.
  CPC ... *B01L 3/502738* (2013.01); *B01L 2200/027* (2013.01); *B01L 2200/028* (2013.01); *B01L 2200/10* (2013.01); *B01L 2300/02* (2013.01); *B01L 2300/087* (2013.01); *B01L 2300/1805* (2013.01); *G01N 2035/00158* (2013.01)

(56) References Cited

U.S. PATENT DOCUMENTS

| | | | |
|---|---|---|---|
| 4,865,584 A | 9/1989 | Epstein et al. | |
| 4,940,527 A | 7/1990 | Kazlauskas et al. | |
| 5,133,937 A | 7/1992 | Frackleton et al. | |
| D351,913 S | 10/1994 | Hieb et al. | |
| 5,585,069 A | 12/1996 | Zanzucchi et al. | |
| 5,587,128 A | 12/1996 | Wilding et al. | |
| 5,599,503 A * | 2/1997 | Manz et al. | 422/82.05 |
| 5,755,942 A * | 5/1998 | Zanzucchi et al. | 506/32 |
| 5,882,903 A | 3/1999 | Andrevski et al. | |
| 5,958,349 A | 9/1999 | Petersen et al. | |
| 6,156,270 A | 12/2000 | Buechler | |
| 6,168,948 B1 | 1/2001 | Anderson et al. | |
| 6,197,595 B1 | 3/2001 | Anderson et al. | |
| 6,382,923 B1 | 5/2002 | Gray | |
| 6,416,293 B1 | 7/2002 | Bouchard et al. | |
| 6,440,725 B1 | 8/2002 | Pourahmadi et al. | |
| 6,565,815 B1 | 5/2003 | Chang et al. | |
| 6,663,359 B2 | 12/2003 | Gray | |
| 6,706,519 B1 * | 3/2004 | Kellogg et al. | 435/287.2 |
| 8,029,733 B2 | 10/2011 | Chang et al. | |
| 2003/0073089 A1 * | 4/2003 | Mauze et al. | 435/6 |
| 2003/0138941 A1 | 7/2003 | Gong et al. | |
| 2003/0224506 A1 | 12/2003 | Agrawal et al. | |
| 2004/0038413 A1 * | 2/2004 | Kramer | 436/63 |
| 2004/0086870 A1 | 5/2004 | Tyvoll et al. | |
| 2004/0087033 A1 | 5/2004 | Schembri | |
| 2004/0161788 A1 * | 8/2004 | Chen et al. | 435/6 |
| 2004/0197233 A1 | 10/2004 | Nagaoka et al. | |
| 2004/0228765 A1 * | 11/2004 | Witty et al. | 422/68.1 |
| 2005/0026277 A1 | 2/2005 | Festoc | |
| 2005/0047973 A1 * | 3/2005 | Schulz | B01L 3/502715 506/33 |
| 2005/0191620 A1 * | 9/2005 | McDevitt | C12Q 1/6816 435/5 |
| 2008/0254532 A1 | 10/2008 | Chang et al. | |

FOREIGN PATENT DOCUMENTS

| | | |
|---|---|---|
| EP | 1464398 A2 | 10/2004 |
| JP | 10-26625 | 1/1998 |
| JP | 2004-504828 | 2/2004 |
| JP | 2004-309145 | 11/2004 |
| WO | 9405414 | 3/1994 |
| WO | 9716561 | 5/1997 |
| WO | 9727324 | 7/1997 |
| WO | 9747967 | 12/1997 |
| WO | 98/38487 | 9/1998 |
| WO | 0241998 A1 | 5/2002 |
| WO | WO2005121963 * | 12/2005 |

OTHER PUBLICATIONS

Pourahmadi et al., "Micro Total Analysis Systems 2000", Proceedings of the µTAS 2000 Symposium, held in Enschede, The Netherlands, May 14-18, 2000, pp. 243-248.
European Opposition of Counterpart European Patent No. 18 96 180 (Eur. Appln. No. 067 65 771.8) (Aug. 23, 2012).
Article entitled The polymerase chain reaction: current and future clinical applications by J. R. Lynch et al., J Med Genet 1999, 27:2-7.
Select pages of Short Protocols in Molecular Biology, Third Edition, by F. M. Ausubel et al. (11 pages).

* cited by examiner

CARTRIDGE, SYSTEM AND METHOD FOR AUTOMATED MEDICAL DIAGNOSTICS

The invention pertains to a cartridge for the detection of the presence, absence or amount of specific DNA or RNA sequences. The invention also pertains to the use of a system, optionally incorporating a cartridge, for the detection of the presence, absence or amount of specific DNA or RNA sequences.

Since the discovery of DNA, the technology relating to the detection of the presence, absence or amount of specific DNA or RNA sequences in a sample has taken an enormous flight. Especially PCR, the Polymerase Chain Reaction has contributed enormously to the development of assays of all types for the detection of the presence or absence of DNA or RNA sequences. At present, it is possible to collect DNA containing samples from an organism and determine the presence, absence or amount therein of certain specific DNA sequences (target sequences). Technology is available to perform such analysis for multiple target sequences at the same time, so-called multiplex detection of target sequences to thereby increase throughput.

At present, this type of analysis is not yet performed on a routine basis, such as for instance the measurement of the blood-glucose content in the case of diabetes. Generally, well-equipped laboratories are necessary, and careful protocols have to be used in order to avoid cross-contamination and to ensure that the results obtained are reliable i.e. false-positive or false-negative readings of the tests are minimized. However, as still a lot of manual labour is involved of extensively trained and supervised personnel, there remains a need in the art to overrcome the above disadvantages of the present methods of DNA or RNA analysis. Especially RNA analysis is known to be very difficult because contamination happens very easy due to the present of minute amounts of RNA in the atmosphere and on the hands of the skilled analysts. Furthermore, the present methods of analysis are not only laborious, they are also time-consuming. Typically, an efficient procedure for a conventional DNA or RNA analysis takes about 6 hours due to, inter alia, all the handling between the various systems for the taking of samples, the isolation of DNA or RNA from the sample, the subsequent assay for the analysis of the presence, absence or amount of the target sequence in the sample, the processing of any results obtained and the corresponding presentation of the results.

Cartridge-based systems for the detection of DNA have been disclosed before.

For example U.S. Pat. No. 5,882,903 discloses a system for the detection of DNA. The system comprises a first assembly having one or more reaction chambers and a second assembly comprising a number of fluid chambers. The fluid chambers each hold fluid which is used during the detection of the DNA. These fluids comprise washing fluids, lysis fluid, and an amplification solution containing an amplification buffer and appropriate primers. The reaction chambers are used to perform the different steps of the detection such as washing, lysis, and amplification.

Other cartridge based systems known from prior art and used for the detection of DNA are for example disclosed in U.S. Pat. No. 5,585,069, U.S. Pat. No. 6,168,948 and WO97/27324.

A disadvantage of the known cartridge-based system is that the cartridges of these systems are designed as a single body. The known cartridge does not offer any flexibility towards the application for which the cartridge is intended to be used, for example for specific bacteria to be detected with the system or for different kinds of samples to be introduced in the cartridge.

It is an object of the present invention to provide a cartridge for the detection of the presence, absence and/or amount of a target nucleotide sequence in a sample, which provides for a more flexible use of such cartridge.

This object is achieved with a cartridge as claimed in claim 1.

By providing a generic part which can be used for a wide variety of applications and one or more application-specific parts which are specifically configured to be used for a certain application, the cartridge can be assembled on the basis of the specific application for which it is intended to be used.

The generic part may typically comprise fluid handling means such as pumps and valves, a number of process chambers which are used independently of the application of the cartridge, and fluid storage and waste rooms for different fluids, such as lysis and washing buffers. These elements of the cartridge will hereinafter be described in more detail.

In an embodiment one of the one or more specific parts is a PCR body having one or more thermocycling chambers and comprising a number of primers. It may be possible that the cartridge is to be used for different panels of bacteria/resistances. By providing different PCR bodies comprising a number of primers, an application-specific PCR body can be chosen on the basis of the application for which the cartridge is used. For instance the PCR body comprising the primers can be selected on the basis of the panels of bacteria/resistances that are to be detected, which selection may be specific for a particular assay or for a particular region, such as Europe, Asia or Africa. It is also possible that the size or the number of thermocycling chambers is selected on the basis of the bacteria/resistances to be detected. In a preferred embodiment the thermocycling chambers are only used for the thermocycling step. The process chambers, in particular the primers, are in such embodiment not affected by any other step performed in the cartridge.

In an embodiment there are provided two or more thermocycling chambers. In each of the thermocycling chambers an amount of process fluid can be brought, which makes an efficient parallel processing possible.

In an embodiment a primer is arranged in each one of the one or more thermocycling chambers. By arranging the primers in the one or more thermocycling chambers the primers do not have to be transferred before the thermocycling steps can be performed. In this way a more efficient use is made of the primers. Furthermore, this allows a more simple design of the PCR body.

In an embodiment the primer is spotted on the PCR body. Such spotting may be done with any known spotting technique, such as for instance ink jet printing. Preferably, the spotted primers are provided in the one or more thermocycling chambers, but they may also be provided in any other suitable location such as the inlet channels for the sample leading to the one or more thermocycling chambers.

In an embodiment one of the one or more application-specific parts is a detection device. A number of different detection methods can be used to detect the amplicons in the sample after the DNA/RNA amplification. Such detection methods may include optical, electrochemical, magnetic cappilary and gel-electrophoresis detection methods. Depending on the detection method to be used for a certain sample the detection device, or at least a part thereof may be selected and connected to the generic part of the cartridge.

In an embodiment the detection device is selected on the basis of the PCR body that is used for the detection of certain bacteria/resistances. Certain detection methods are typically related to the specific bacteria/resistances which are to be detected, and therewith also with the primers which are used in the detection method. As a result the PCR body with primers and the detection device may be selected as a pair, i.e. with the section of a PCR body also the selection of the detection device is made.

It may be possible that only a particular part of the detection device, such as a substrate and/or substrate holder may be specific for the detection of a certain DNA/RNA. It is therefore contemplated that the application-specific detection device may only be a part of the actual detection system used in the cartridge to make the detection of a particular DNA/RNA possible.

In an embodiment of the invention one of the one or more application-specific parts is a sample introduction device. Dependent on the quantity of the sample needed, the type of sample, the state in which it is provided, different sample introduction devices may be used for introduction of a sample into the cartridge. The use of sample introduction device further provides an easy and secure connection to the cartridge, and therewith an easy and reliable introduction of the sample in the cartridge.

In an embodiment the sample introduction device is a pre-lysis device configured to prepare a sample to a specific state. The generic part of the cartridge is designed to process a sample in a particular sample state, for instance fluid. A pre-lysis device may be provided to process the sample from a particular state in which it is available, and in which it can not be used in the cartridge, to the state for which the cartridge is designed to process it. Such state may be to which is dried out fluid, fluid being present in a solid carrier, and such. The process in the pre-lysis may be performed before the pre-lysis device is connected to the generic part, but also after that this connection is made.

In an embodiment at least one of the one or more of the application-specific parts is provided with an identification device. To avoid errors in the selection of the application specific parts it is useful to provide an identification on the application-specific parts so that easily can be checked whether the correct application-specific part or set of parts is combined with the generic part.

Such identification device may include stickers, bar codes, color codes, magnetic codes and such. Preferably, a automatic identification system, such as a RF-tag identification system, is used. Such more advanced identification devices may also be used to track the location history of the generic part and/or the application specific parts. It may for instance be important that a certain application-specific part is cooled. With the use of a location history track system it can be checked whether the application-specific part has not been too long out of a cooling device. In a preferred embodiment a control unit of the detection system checks whether the correct application-specific parts have been connected with the general part and whether the generic part and application specific parts still fulfill all requirements regarding location history and such.

The present invention typically avoids or minimizes manual labour, avoids cross contamination, provides faster results that are more reliable, is user friendly and is easily adapted for the analysis of different target sequences. The present invention provides for a high throughput method for the analysis for the presence, absence or amount of DNA or RNA in any type of sample, preferably blood.

The present invention provides for a cartridge that is suitable for the detection of the presence, absence or amount of DNA and/or RNA. The detection of the presence, absence or amount of DNA and/or RNA is indicative, for instance, for the presence, absence or amount of a gene, an allele of a gene, a genetic trait or disorder, a polymorphism, a single nucleotide polymorphism (SNP) or of the presence of exogenous DNA or RNA in an organism, i.e. the presence, absence or amount of pathogens or bacteria in organisms.

Through the present invention, suitable remedies can be developed for the preparation of medicaments for the treatment of the so diagnosed ailment. For instance, the detection in a sample (say, blood) from an organism (say, a human) of a pathogen (say, a virus) may thus lead to the diagnosis and the corresponding treatment (say, an antibiotic).

The cartridge may be of an exchangeable type which can be positioned in a reusable apparatus. Such cartridge may be disposable, recyclable or reusable, possibly after cleaning. By providing an exchangeable cartridge all parts that may come into contact with the sample may after the detection process be taken out of the apparatus and the cartridge may be exchanged for another one or cleaned before a next use. In other embodiments the cartridge may be an integral part of the reusable apparatus which is cleaned after each use.

In certain embodiments the apparatus comprises a control unit for controlling the isolation means, amplification means and/or the detection means. The control unit makes a automatic control of the isolation of DNA, the amplification of DNA and the detection of the amplified DNA possible.

The cartridge comprises one or more chambers in which the sample is held during the detection process. Such chambers may comprise an introduction chamber for introducing a sample in the cartridge, a lysis chamber for lysis of the cells in the sample, a washing chamber for washing, one or more thermocycling chambers for the amplification of the DNA, and a detection chamber which makes detection possible. It is also possible to provide a single chamber for one or more of the functions described in relation to the chambers. In such embodiment two or more chambers of the introduction chamber, lysis chamber, washing chamber, the thermocycling chamber(s), and the detection chamber may be combined in one single chamber.

During the different steps of the detection process the sample will be in a respective chamber. For this purpose, the sample will be transferred from one chamber to another chamber between two process steps. To make such transfer possible, each chamber is at least connected with another chamber by a fluid channel. In at least one, but preferably each of these fluid channels a valve means may be provided, which valve means preferably normally closes the fluid channel, but opens the fluid channel upon actuation of the valve means therewith placing the respective two chambers in fluid communication. The valve means may be designed as a one-way valve.

In certain embodiments the valve means are actuated by a valve actuation device. This valve actuation device is preferably arranged in the reusable apparatus.

In certain embodiments pump means are provided to pump the sample or any other fluid used in the detection process such as lysis buffer, reagents, washing and separation buffers, pre-amplification buffers, from one chamber to another chamber. These pump means may be actuated by pump actuation means which are preferably arranged in the reusable apparatus.

In certain embodiments, the system comprises means for data collection and/or means for data processing. These means are intended for use in the analysis of the detected DNA and/or for the interpretation of the results. In particular, in certain embodiments the data processing means that are able to link the presence, absence or amount of the target nucleic acid (or combination thereof) to a particular diagnosis. Such a data processing means can for example be in the form of a computer in combination with a database.

In certain embodiments, the system can also comprise the means for the introduction of one or more samples. Such sample introduction means may comprise any suitable device, such as a holding or docking device for the introduction of a sample from a syringe or pipette or such and may for instance comprise a one-way inlet valve, a septum, filters, and an overflow.

In certain embodiments, the system can also comprise lysis device. In the lysis device, that can be under the control of a control unit, the sample is treated to provide any nucleic acids in the sample in a form that they can be isolated from the sample. This lysis step typically includes the lysis of the cells such that cell and/or nuclear membranes are ruptured to thereby free the nucleic acids contained therein. Use can be made of means of physical or mechanical manipulation for the lysis step, but also chemical means can be used for lysis of the cells in the sample, such as a lysis buffer. Means for mixing can be provided to mix the sample and the lysis buffer Methods for lysis of cells are well known in the art from textbooks etc. If necessary such methods can be adapted for use in the present system. Any waste that is produced by the lysis step can be discarded, for instance to a waste device.

In certain embodiments, the sample insertion device and the lysis device can be combined.

In certain embodiments, the system can also comprise an enrichment device, optionally under the control of a control unit. The enrichment device enables the isolation of DNA from the lysed sample. To this end the enrichment device may be equipped with means for the isolation of DNA, such as magnetic particles. In this embodiment, the DNA or RNA of the present invention is absorbed onto magnetic particles. The absorbed nucleic acid material can be subjected to one or more washing, draining and/or purifying steps to remove any unwanted material such as remains of biological material contained in the sample and other sample components that are not DNA and/or RNA. When the absorbed DNA or RNA is of a desired purity, it can be desorbed or eluted from the magnetic particles. The enrichment device can also be equipped with means for physical or mechanical manipulation of the fluids for mixing, separating and isolating the DNA or RNA.

In certain embodiments, the system can also comprise the reagents that are necessary for the enrichment step, i.e. the isolation of the DNA or RNA, such as buffers, washing fluids, water, filters, magnetic beads etc.

In certain embodiments, the system can also comprise a waste device to accommodate any waste produced from the enrichment step such as used buffers, washing fluids and the like.

In certain embodiments, the different waste devices of the system can be separate for each different purpose or volume. In certain embodiments, two or more of the waste devices described herein can be combined to accommodate all waste that is produced by the method of the present invention.

In certain embodiments, the system further comprises a pre-amplification device, optionally under the control of a control unit. The pre-amplification device can be used, for instance for increasing the total amount of DNA or RNA to be analyzed. Subjecting DNA or RNA obtained from the isolation step to a pre-amplification step can increase the total amount of DNA. This is advantageously, especially in the case of multiplex analysis, where multiple tests are performed on the isolated DNA, for instance to detect the presence absence or amount of multiple pathogens in one sample at a time. Suitable technology is available in the art for increasing the amount of DNA and is generally known as Whole Genome Amplification.

In the pre-amplification device, the isolated and purified DNA or RNA can be pre-treated with, inter alia an pre-amplification buffer and in case of whole genome amplification, with enzymes and DNTPs. The pre-amplification device can be connected to a waste device for the disposal of materials.

In certain embodiments, the pre-amplification device can also be used for carrying out certain assays for the detection of specific nucleic acids. Examples thereof are OLA-PCR like technologies such as provided by Applera (SNPplex), Keygene (SNPWave) and MRC-Holland (MPLA).

In certain embodiments, the system comprises an amplification device. The amplification device can be under the control of a control unit. The isolated DNA, optionally pre-treated as described herein elsewhere, is subjected in the amplification device to an amplification treatment in the amplification device. The amplification treatment comprises bringing the isolated DNA in contact with a set of PCR primers that are specific for the target nucleic acid, PCR enzymes such as one or more polymerases and dNTPs.

In certain embodiments, the amplification device holds a plurality of chambers. The plurality of chambers enables the isolated or pre-amplified DNA or RNA to be divided in portions and distributed amongst the chambers. In each chamber, an amplification step can be performed using a different set of primers. In this manner, multiplex analysis is provided in that one sample can be analyzed for the presence, absence or amount of different target nucleic acids. IN the case of multiplex analysis, the primer set for each target nucleic acid can be equipped with a detectably different label, i.e. with a different fluorescent spectrum.

In certain embodiments, the system can also comprise reagents for the amplification of the isolated DNA such as enzymes, DNTPs etc.

In certain embodiments, the system can also comprise a detection device. The detection device can be under the control of a control unit. The detection device is suitable for the detection of the amplified DNA or RNA and preferably for the detection of the labels that are incorporated in the amplification products.

The detection device may detect based on label, length, mobility, nucleotide sequence, mass or a combination thereof. In certain embodiments a detection device can detect based on optical, electrochemical, magnetic or mobility (gel-electrophoresis). In principle any suitable detection device known from prior art may be used.

In certain embodiments, the system also comprises a data collection device to collect data obtained from the detection device.

In certain embodiments, the system also comprises a data processing device to process the data.

In one aspect of the present invention, there is provided a method for the detection of the presence, absence and/or amount of a target nucleotide sequence in a sample comprising one or more nucleic acid sequences, wherein the method comprises the steps of:

providing a sample from an organism;
performing steps for isolation of the nucleic acid sequences from the sample;

performing steps for amplification of (part of) the nucleic acid sequences to thereby provide amplicons;
detecting the presence, absence and/or amount of the amplicons corresponding to the target nucleotide sequence amongst the nucleic acid sequences in the sample.

In certain embodiments, the method is performed in a cartridge as defined in the present application.

In certain embodiments, the target nucleotide sequence can be selected from the group consisting of DNA, genomic DNA, RNA, mRNA, cDNA, transgenic DNA, ETC.

In certain embodiments, the organism is a human, a non-human animal, a micro-organism or a plant.

In certain embodiments, the sample is tissue, bodily fluids such as sputum, semen, blood, urine, and/or faces.

In certain embodiments, the target nucleotide sequence is an exogenous sequence.

In certain embodiments, the target nucleic sequence is a pathogen.

In certain embodiments, the sample comprising the nucleic acid sequences is subjected to lysis to free the contained nucleic acid sequences. In certain embodiments, the lysed sample is subjected to a sequence of washing and collecting steps as are themselves known in the art and described in standard text books that aim at the isolation of the nucleic acids from the sample. These steps can be performed in a single step or as a sequence of multiple steps. After isolation of the nucleic acids from the sample, the nucleic acids can be subjected to an amplification reaction using primers that are selective for the detection of the target nucleic acid.

Nucleic acid amplification methods usually employ two primers, dNTPs, and a (DNA) polymerase. A preferred method for amplification is PCR. "PCR" or "Polymerase Chain Reaction" is a rapid procedure for in vitro enzymatic amplification of a specific DNA segrnent. The DNA to be amplified is denatured by heating the sample. In the presence of DNA polymerase and excess deoxynucleotide triphosphates, oligonucleotides that hybridise specifically to the target sequence prime new DNA synthesis. One round of synthesis results in new strands of determinate length, which, like the parental strands, can hybridise to the primers upon denaturation and annealing. The second cycle of denaturation, annealing and synthesis produces two single-stranded products that together compose a discrete double-stranded product, exactly the length between the primer ends. This discrete product accumulates exponentially with each successive round of amplification. Over the course of about 20 to 30 cycles, many million-fold amplification of the discrete fragment can be achieved. PCR protocols are well known in the art, and are described in standard laboratory textbooks, e. g. Ausubel etal., Current Protocols in Molecular Biology, John Wiley & Sons, Inc. (1995). Other multiplex and/or isothermal amplification methods that may be applied include e. g. LCR, self-sustained sequence replication (3SR),Q-β-replicase mediated RNA amplification, rolling circle amplification (RCA) or strand displacement amplification (SDA).

Detection of the labelled amplicons is performed by a detector to result in detection data. The detector is of course dependent on the general system with which the discrimination between the amplicons of the target sequences is performed but is also depending on the label that is present on the primer, such as a fluorescent or a phosphorescent label. To discriminate between different target sequences in the sample preferably a difference in fluorescence spectrum of the respective corresponding amplicons is used. In certain embodiments, at least one of the primers comprises a label, preferably the forward primer comprises a label. The label can be selected from a large group, amongst others comprising fluorescent and/or phosphorescent moieties such as dyes, chromophores, or enzymes, antigens, heavy metals, magnetic probes, phosphorescent moieties, radioactive labels, chemiluminescent moieties or electrochemical detecting moieties. In certain embodiments the label is a fluorescent or phosphorescent dye. Examples of such dyes are FAM, HEX, TET, JOE, NED, and (ET-) ROX. Dyes such as FITC, Cy2, Texas Red, TAMPA, Alexa fluor 488™, BodipyFL, Rhodamine 123, R6G, Bodipy 530, Alexafluor™532.

By using different primer sets each containing a different label, the number of target sequences that can be discriminated in a sample and hence the number of target sequences in a sample that can be detected can be increased by using additional labels. The maximum number of labels that can be used in one sample in a multiplex method is governed mostly by the limitations in the detection capabilities of the available detection platforms.

In certain embodiments, the amplification is performed using the Polymerase Chain Reaction with at least one forward and at least one reverse primer that are selective for the target sequence and not for any other sequence in the sample.

In certain embodiments, at least one of either the forward or the reverse primer is labelled.

In certain embodiments, the amplification step is preceded or replaced by an assay for the detection of nucleic acids in samples.

In certain embodiments, the amplicons are detected based on label, length, mobility, nucleotide sequence, mass or a combination thereof.

In certain embodiments, the amplicons are detected based on optical, electrochemical, or magnetic detection.

The invention also provides for a cartridge for the detection of the presence, absence and/or amount of a target nucleotide sequence in a sample comprising one or more nucleic acid sequences, wherein the cartridge comprises a generic part. The generic part comprises pumps, valves, process chambers, and fluid and waste rooms. One or more separate application-specific parts are each specifically configured for a specific application. The one or more application-specific parts are separately connectable to the generic part. At least one of the one or more separate application-specific parts is a PCR body comprising at least one thermocycling chamber and plural primers. A click-fit connection is provided between at least one of the one or more application-specific parts and the generic part.

In embodiments, at least one primer is arranged in each one of the one or more thermocycling chambers. In embodiments, at least one of the primers is spotted on the PCR body. In embodiments, the PCR body is disc-shaped. In embodiments, the PCR body comprises one or more thermal masses. In embodiments, one of the one or more application-specific parts is a detection device. In embodiments, the detection device is selected on the basis of the primers in the PCR body. In embodiments, one of the one or more application-specific parts is a sample introduction device configured to prepare a sample to a specific state. In embodiments, the sample introduction device is a pre-lysis device configured to prepare a sample to a specific state. In embodiments, the cartridge further comprises spaces for holding a sample or part thereof in each of the generic part and the one or more application-specific parts, wherein each space for holding the sample or part thereof is air-tight. In embodiments, at least one of the one or more of the application-specific parts is provided with an identification device. In embodiments, each of the one or more application-specific parts and the generic part is provided with an identification device.

The invention also provides for a cartridge for the detection of the presence, absence and/or amount of a target nucleotide sequence in a sample comprising one or more nucleic acid sequences, wherein the cartridge comprises a generic part. The generic part comprises pumps, valves, process chambers, and fluid and waste rooms. Plural different application-specific parts are separate from the generic par. The plural different application-specific parts are separately connectable to different portions of the generic part. At least one of the plural different application-specific parts being a PCR body comprising at least one thermocycling chamber and plural primers, In embodiments, at least one primer is arranged in each one of the one or more thermocycling chambers. In embodiments, at least one of the primers is spotted on the PCR body. In embodiments, the PCR body is disc-shaped. In embodiments, the PCR body comprises one or more thermal masses. In embodiments, one of the one or more application-specific parts is a detection device. In embodiments, the detection device is selected on the basis of the primers in the PCR body. In embodiments, one of the one or more application-specific parts is a sample introduction device configured to prepare a sample to a specific state. In embodiments, the sample introduction device is a pre-lysis device configured to prepare a sample to a specific state. In embodiments, the cartridge further comprises spaces for holding a sample or part thereof in each of the generic part and the one or more application-specific parts, wherein each space for holding the sample or part thereof is air-tight. In embodiments, at least one of the one or more of the application-specific parts is provided with an identification device. In embodiments, each of the one or more application-specific parts and the generic part is provided with an identification device.

The invention also includes a cartridge for the detection of the presence, absence and/or amount of a target nucleotide sequence in a sample comprising one or more nucleic acid sequences, comprising a generic part, the generic part comprising a click-fit connector, pumps, valves, process chambers, and fluid and waste rooms, one or more separate application-specific parts, each being specifically configured for a specific application, the one or more application-specific parts being separately connectable to the generic part, and at least one of the one or more separate application-specific parts being a PCR body comprising one or more thermocycling chambers and plural primers, wherein the one or more thermocycling chambers of the PCR body contains the plural primers for PCR amplification prior to the sample being introduced into the cartridge, wherein at least one of the one or more application-specific parts is click-fit connected to the generic part via the click-fit connector, wherein at least one of the primers is spotted on the PCR body, and wherein the cartridge is configured to be removably connected to an apparatus comprising one or more actuation devices that can actuate one or more elements of the cartridge.

The invention also includes a cartridge for the detection of the presence, absence and/or amount of a target nucleotide sequence in a sample comprising one or more nucleic acid sequences, comprising a generic part, the generic part comprising a releasable click-fit connector, pumps, valves, process chambers, and fluid and waste rooms, plural separate application-specific parts, each being specifically configured for a specific application, the application-specific parts being separately connectable to the generic part, at least one of the separate application-specific parts being a detection device connectable to the generic part, and at least one of the separate application-specific parts being a circular, disc-shaped PCR body comprising one or more thermocycling chambers and plural primers, wherein the one or more thermocycling chambers of the PCR body contains the plural primers for PCR amplification prior to the sample being introduced into the cartridge, wherein at least one of the one or more application-specific parts is click-fit connected to the generic part via the click-fit connector, wherein the PCR body comprises one or more thermal masses, and wherein the cartridge is configured to be removably connected to an apparatus comprising one or more actuation devices that can actuate one or more elements of the cartridge.

The invention also includes a cartridge for the detection of the presence, absence and/or amount of a target nucleotide sequence in a sample comprising one or more nucleic acid sequences, comprising a generic part, the generic part comprising at least one click-fit connector, pumps, valves, process chambers, and fluid and waste rooms, one or more separate application-specific parts, each being specifically configured for a specific application, the one or more application-specific parts being separately connectable to the generic part, at least one of the one or more separate application-specific parts being a PCR body comprising one or more thermocycling chambers and plural primers, and a detection device, wherein the one or more thermocycling chambers of the PCR body contains the plural primers for PCR amplification prior to the sample being introduced into the cartridge and prior to the PCR body being connected to the generic part, wherein a releasable click-fit connection is provided between the PCR body and the generic part, wherein the detection device is specifically configured to perform detection with the primers in the PCR body, and wherein the cartridge is configured to be removably connected to an apparatus comprising one or more actuation devices that can actuate one or more elements of the cartridge.

The invention also includes a cartridge for the detection of the presence, absence and/or amount of a target nucleotide sequence in a sample comprising one or more nucleic acid sequences, the cartridge comprising a generic part, the generic part comprising a click-fit connector, pumps, valves, process chambers, and fluid and waste rooms, plural different application-specific parts separate from the generic part, the plural different application-specific parts being separately connectable to different portions of the generic part, and at least one of the plural different application-specific parts being a PCR body comprising one or more thermocycling chambers and plural primers, wherein the one or more themiocycling chambers of the PCR body contains the plural primers for PCR amplification prior to the PCR body being connected to the generic part, and wherein the cartridge is configured to be removably connected to an apparatus comprising one or more actuation devices that can actuate one or more elements of the cartridge.

The invention also includes a cartridge for detecting a presence, absence and/or amount of a target nucleotide sequence in a sample comprising one or more nucleic acid sequences, the cartridge comprising a generic part comprising a click-fit connector, an identification and a plurality of different devices arranged inside a body of the generic part, a first application-specific part comprising an identification and being connectable to the generic part, a second application-specific part comprising an identification and being connectable to the generic part, the first application-specific part being different from the second application-specific part and the first application-specific part comprising a PCR body containing amplification chambers and primers contained in the amplification chambers for PCR amplification, and the primers being contained within the amplification chambers prior to the first application-specific part being connected to the generic part, wherein the first part is connected to the generic part via the click-fit connector arranged on the generic part and the second part is connected to the generic part at a location on the generic part that is spaced from the click-fit connector, and wherein the cartridge is configured to be removably connected to an apparatus comprising one or more actuation devices that can actuate one or more elements of the cartridge.

FIG. 2 shows a schematic block diagram of the architecture of an embodiment of the system according to the invention;

Figure 1:
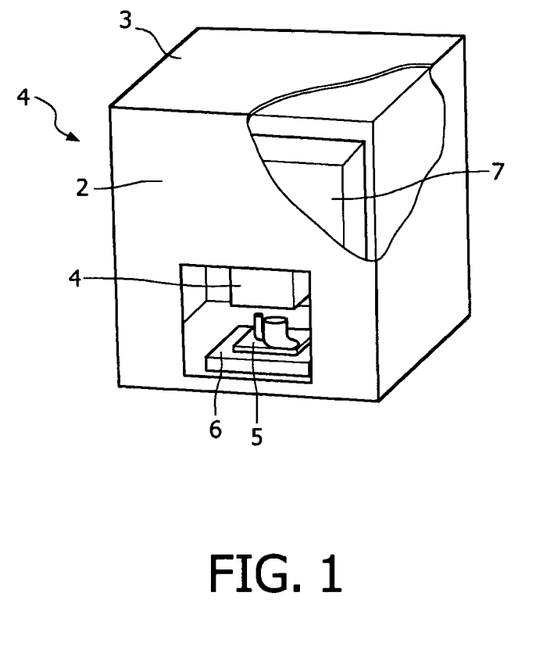
FIG. 1 shows a perspective view of a system according to an embodiment of the invention.

FIG. 1 shows an embodiment of a system for the detection of the presence, absence and/or amount of a target nucleotide sequence in a sample comprising one or more nucleic acid sequences, in general indicated with the reference numeral 1. The system comprises a reusable apparatus 2 with a housing 3 (partly broken away).

In the apparatus 2 a recess 4 is provided. An exchangeable cartridge 5 is removably positioned in this recess 4. The cartridge 5 may be reusable, recyclable or disposable.

In order to make detection possible the cartridge 5 comprises introduction means for the introduction of a sample, isolation means for the isolation of DNA, amplification means for the amplification of DNA, and detection means for the detection of amplified DNA. The introduction means, isolation means, amplification means and/or detection means may be arranged on the cartridge and/or in the reusable apparatus. In general it is preferred to arrange in the apparatus 2 all parts of the system 1 which normally do not come into contact with the sample. The sample is held throughout the detection process in cartridge which works as a cartridge.

Hereinafter a preferred embodiment of the arrangement of the introduction means, isolation means, amplification means and/or detection means is described. However, other embodiments are also possible.

The apparatus 2 comprises a control unit 7 for automatically controlling the different steps of the detection process as will be described hereinafter.

Further, the apparatus 2 comprises one or more actuation devices for the actuation of different elements arranged on the cartridge. These actuation devices may comprise one or more pump means actuation devices for the actuation of one or more pump means for pumping fluid, one or more valve actuation devices for actuation of one or more valves being arranged in a fluid channel in the cartridge, and other actuation devices such as mechanical actuation devices for providing, for example, a rotary or translating movement to one or more parts of the cartridge.

In the apparatus a detection device is provided which may detect the presence, absence and/or amount of DNA. For this purpose the DNA may be placed in a detection chamber which is arranged on the cartridge. The detection device may work on an optical, electrochemical, or magnetic principle as known from prior art. Any other suitable detection method may be applied.

The apparatus may further comprise a data collection device and a data processing device to collect data obtained from the detection device and to process these data, respectively.

The apparatus 2 comprises a carrier 6 for supporting the cartridge 5. The carrier 6 is movable in a vertical direction between a lower position (in which the carrier is shown) and a higher position. In the lower position the cartridge 5 can be placed on or taken from the carrier 6. The higher position is the working position in which the cartridge 5 is positioned during the detection process. In this higher position the cartridge is clamped between the carrier 6 and the a number of devices being arranged on the cartridge, such as pump means, valves, mechanical means, and a detection chamber may cooperate with corresponding devices being arranged in the apparatus 2, such as pump means, valve and other mechanical actuation devices, and a detection device.

In an alternative embodiment it is also possible that a part of the apparatus 2 comprising the corresponding devices can be moved towards and away from a cartridge placed in the apparatus 2.

In FIG. 2 a schematic block diagram is shown in which the different process steps of the detection process using the method according the present invention are shown. This diagram is used to explain the main architecture of the cartridge 5 and the relation between the apparatus 2 and the cartridge 5.

In a first step ("sample insertion") a sample is introduced in the cartridge 5. For this purpose the cartridge 5 comprises an introduction device with which a sample can be introduced in the cartridge 5. The introduction device may for example be any suitable device for the introduction of a sample from a syringe or pipette or such, and may comprise a holding or docking device, a one-way inlet valve, a septum, filters, and an overflow. After introduction of the sample this sample may be guided to an introduction chamber.

In a second step ("lysis") the sample is treated to provide any nucleic acids in the sample in a form that they can be isolated from the sample. This lysis step typically includes the lysis of the cells such that cell and/or nuclear membranes are ruptured to thereby free the nucleic acids contained therein. The lysis step is carried out in a lysis chamber which is part of a lysis device. This lysis chamber is in fluid communication with the introduction device for the sample, for instance by means of a fluid channel. Pumping means may be provided for pumping the sample from the introduction chamber to the lysis chamber.

In a preferred embodiment the introduction chamber and lysis chamber are the same chamber.

In an embodiment the lysis device comprises a physical or mechanical manipulation means for the lysis step. In another embodiment, or the same embodiment, (also) chemical means can be used for lysis of the cells in the sample, such as a lysis buffer. Such lysis buffer may be held before use in a separate lysis buffer container which is in fluid communication with the lysis chamber. A valve, preferably a one-way valve, may be provided in the fluid channel connecting the lysis buffer container and the lysis chamber.

Means for mixing can be provided to mix the sample and the lysis buffer. These mixing means may be actuated by the apparatus.

The lysis and possibly the mixing is carried out under control of the control unit of the apparatus 2. The valves and pump means are actuated by the valve and pump means actuation devices being arranged in the apparatus 2.

Any waste fluid that is produced by the lysis step can be discarded, for instance to a waste device which may be present in the cartridge. Such waste device may be embodied as a waste chamber which is in fluid communication with the lysis chamber.

In a third step ("enrichment"), an enrichment device, being arranged in the cartridge, enables the isolation of DNA from the lysed sample. To this end the enrichment device may be equipped with means for the isolation of DNA, such as magnetic particles.

The enrichment step is carried out in an enrichment chamber which is in fluid communication with the lysis chamber. In the fluid channel between lysis chamber and enrichment chamber a valve is provided to make it possible that only a flow through the fluid channel is possible when required. The valve may be actuable by the valve actuation means provided in the apparatus.

In this embodiment, the DNA or RNA of the present invention is absorbed onto magnetic particles. The absorbed nucleic acid material can be subjected to one or more washing, draining and/or purifying steps to remove any unwanted material such as remains of biological material contained in the sample and other sample components that are not DNA and/or RNA. This washing and purifying step is shown as a fourth step "washing and purifying" in FIG. 2. However, the "washing and purifying" step can also be regarded as a part of the "enrichment" step. When the absorbed DNA or RNA is of a desired purity, it can be desorbed or eluted from the magnetic particles. The washing and purifying step is carried out in a washing chamber. In the present embodiment this washing chamber is the same as the enrichment chamber. However, in other embodiments a separate chamber may be provided.

The cartridge 5 is provided with one or more washing buffer and elution buffer containers for holding the washing buffer(s) and elution buffer(s), respectively. Each of these washing buffer and elution buffer containers is in fluid communication with the washing chamber, and again each of the fluid channels providing this fluid communication is provided with a valve, preferably a one-way valve. Similar containers may be provided for any other reagents that are necessary for the enrichment step, i.e. the isolation of the DNA or RNA.

The valves of the enrichment device are actuated by the valve actuation device of the apparatus 2 and may be under control of the control unit 7.

In an alternative embodiment the enrichment device can also be equipped with physical or mechanical manipulation means of the fluids for mixing, separating and isolating the DNA or RNA. Such physical or mechanical manipulation means may be actuated by an actuation device of the apparatus 2 and may be under control of the control unit 7 of the apparatus.

Any waste produced from the enrichment step such as used buffers, washing fluids and the like can be guided to a waste device. This waste device which is part of the cartridge may be the same waste device as the waste device described in the lysis device. As an alternative, the waste devices of the lysis step and the enrichment step can be separate for each different purpose or volume.

In a fifth step ("pre-amplification") the total amount of DNA or RNA to be analyzed may be increased by the use of a pre-amplification device. Subjecting DNA or RNA obtained from the isolation step to a pre-amplification step can increase the total amount of DNA. This is advantageously, especially in the case of multiplex analysis, where multiple tests are performed on the isolated DNA, for instance to detect the presence absence or amount of multiple pathogens in one sample at a time.

The pre-amplification device comprises a pre-amplification chamber in which the pre-amplification is carried out. The preamplification chamber may be the same chamber as or a different chamber than the enrichment chamber and/or washing chamber. The pre-amplification device is under the control of the control unit 7.

In the pre-amplification device, the isolated and purified DNA or RNA can be pre-treated with, inter alia an pre-amplification buffer and in case of whole genome amplification, with enzymes and DNTPs. Before use this pre-amplification buffer is held in a buffer container which is in fluid communication with the previous process chamber, for instance the washing chamber. A valve may in the fluid channel providing the fluid communication.

The pre-amplification device can be connected to a waste device for the disposal of materials.

In a sixth step ("amplification") the isolated DNA, optionally pre-treated as described herein elsewhere, is subjected in the amplification device to an amplification treatment. The amplification treatment comprises bringing the isolated DNA in contact with a set of PCR primers that are specific for the target nucleic acid, PCR enzymes such as one or more polymerases and dNTPs.

For this purpose the amplification device comprises a plurality of amplification chambers. The plurality of amplification chambers enables the isolated or pre-amplified DNA or RNA to be divided in portions and distributed amongst the chambers. In each chamber, an amplification step can be performed using a different set of primers. In this manner, multiplex analysis is provided in that one sample can be analyzed for the presence, absence or amount of different target nucleic acids. In the case of multiplex analysis, the primer set for each target nucleic acid can be equipped with a detectably different label, i.e. with a different fluorescent spectrum.

The cartridge may comprise reagents containers for holding reagents for the amplification of the isolated DNA such as enzymes, DNTPs etc.

In a final step ("detection") the amplified DNA or RNA and preferably the labels that are incorporated in the amplification products are detected. For this purpose the system 1 comprises a detection device. This detection device comprises a detection chamber which is arranged on the cartridge 5. Other parts of the detection device may be arranged in the reusable apparatus 2 as described herein above. The detection chamber is in fluid communication with the one or more amplification chambers for simultaneously or subsequently introducing the DNA or RNA out of the one or more amplification chambers. Valves may be provided in the fluid channel connecting the detection chamber with the one or more amplification chambers.

The detection device can be under the control of the control unit 7. The detection device may detect based on label, length, mobility, nucleotide sequence, mass or a combination thereof. In certain embodiments a detection device can detect based on optical, electrochemical, magnetic or mobility (gel-electrophoresis). In principle any suitable detection device known from prior art may be used.

The detected information may be collected by data collection means and processed by data processing means to come for instance to a certain diagnose.

All fluid flows within the cartridge may be obtained by pump means which are provided in the cartridge. Such pump means may work on the basis of compressing or expanding spaces in the cartridge, in particular the spaces of the respective process chambers, i.e. the introduction chamber, the lysis chamber, the pre-amplification chamber, the washing and purifying chamber, the amplification chamber the and detection chamber, and the respective reagents containers. These pump means may also be of any other suitable type.

The pump means in the cartridge are actuated by the pump means actuation devices provided in the apparatus 2. These pump means actuation devices are under control of the control unit 7.

In the fluid paths or channels between the different process chambers i.e. the introduction chamber, the lysis chamber, the pre-amplification chamber, the washing and purifying chamber, the amplification chamber the and detection chamber, and the respective reagents containers, valves may be provided to only allow a flow when required. As most fluid will pass the fluid channels only in one direction the valves are preferably one-way valves.

The valves may be actuated by valve actuation devices which preferably are arranged in the apparatus 2.

All steps as described above may be under control of the control unit 7.

Figure 3:
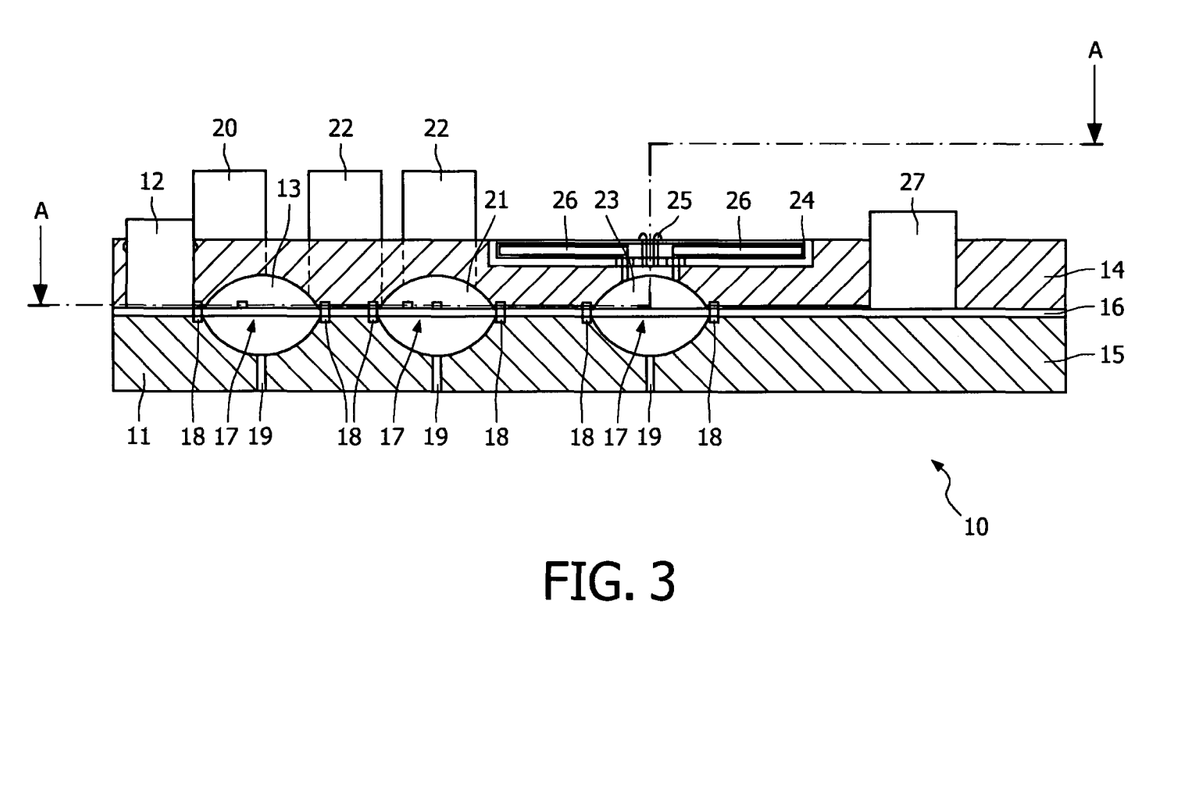
FIG. 3 shows a schematic cross section (B-B in FIG. 4) of an embodiment of a cartridge according to the present invention.
Figure 4:
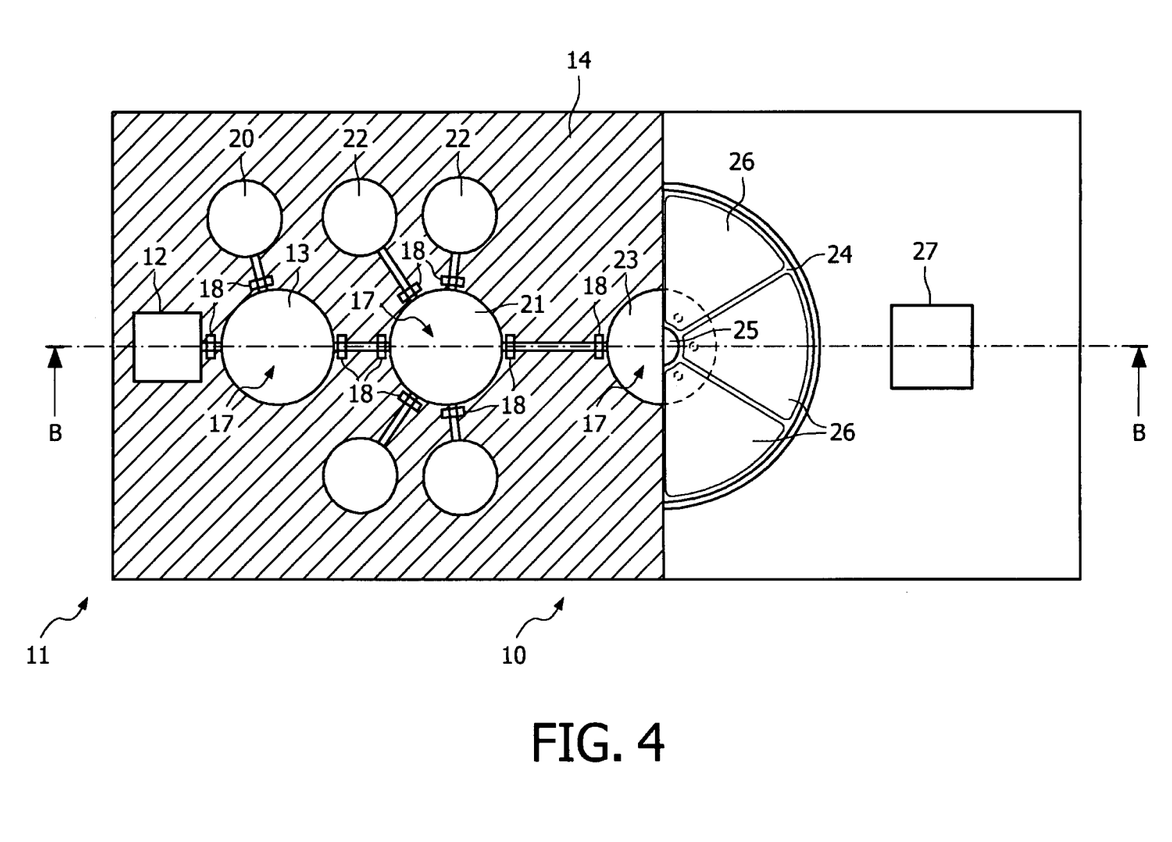
FIG. 4 shows a schematic top view/cross section (A-A in FIG. 3) of the embodiment of FIG. 3.

FIGS. 3 and 4 show in more detail an embodiment of a cartridge generally indicated with the reference numeral 10, in which the method as described above can be performed. The cartridge comprises a generic part 11 having a number of process chambers, and fluid handling systems as will be described hereinafter.

The different parts of the cartridge 10 will hereinafter be described in the order in which they will be used when a detection method for detection of the presence, absence and/or amount of a target nucleotide sequence in a sample comprising one or more nucleic acid sequences is performed.

The first application-specific part which is comprised in the cartridge 10 is a pre-lysis device 12. This pre-lysis device 12 is configured to process a sample to a certain state which can be processed by the cartridge 10.

For example the sample may be provided in a solid state, for instance dried out blood, while the cartridge is designed to process a sample in a fluid state. In such case the sample has to be brought into a fluid state before it can be processed in the cartridge. Such processing may be performed by providing suitable enzymes in a suitable medium in the pre-lysis device 12. Such processes are known in the art, such as for example trypsinization. By providing a pre-lysis device which can be connected to the generic part 11, the processing of the sample to the desired state can be performed without the need of transferring the sample after processing thereof therewith avoiding any chance on contamination. The processing of the sample to the desired state may be performed before or after that the pre-lysis device is connected to the generic part 11.

When no processing of the sample is needed, as the sample is already in a state which can be processed by the cartridge, the pre-lysis-device may also be indicated as a sample introduction device. The sample introduction device is then used to introduce the sample into the cartridge without risking any contamination, as the sample introduction device is designed to be connected to the generic part 11 for the introduction of the sample in the cartridge 10.

When the sample is introduced in the cartridge 10, it may be pumped to the lysis chamber 13. The generic part 11 of the cartridge 10 comprises fluid handling means including pumps and valves for pumping the sample to the different process chambers. In general the generic part 11 comprises two main components 14, 15 which are placed against each other with interposition of a flexible membrane 16. The two main components 14, 15 comprise recesses which together with the flexible membrane 16 may form pump chambers, valves, fluid channels, fluid storage stations and such.

In the cartridge shown in the drawings the sample will mainly be kept above the flexible membrane, while pumps 17 and valves 18 are mainly actuated from the bottom side of the flexible membrane 16. Fluid can be pumped in or out of a chamber by moving the flexible membrane to increase or decrease the space within the chamber, respectively. The flexible membrane can for example be moved by introducing air or fluid into the space between the flexible membrane 16 and the component 15. The air or fluid may be introduced through the channels 19. The other pump chambers may also be used as pump chambers in a corresponding way. Other means for moving the flexible membrane such as mechanical actuators may also be used. The valves may be actuated by air or fluid pressure, mechanical actuation or any other suitable actuation device. The movement of the flexible membrane 16 with respect to the component 14 may also be used to open and close a valve seat, whereby for example in the closed position of a valve the flexible membrane 16 is held against a channel end of the component 14.

In itself, such cartridge based systems having the type of pumps 17 and valves 18 for the handling of fluids as described, have been disclosed before, however, but not for the purpose of the present invention. Reference is made, inter alia, to U.S. Pat. No. 6,156,270, USD37164, USD 351913, U.S. Pat. No. 6,382,923, U.S. Pat. No. 6,663,359, U.S. Pat. No. 6,416,293, U.S. Pat. No. 4,865,584 and U.S. Pat. No. 4,479,760.

In the lysis chamber 13 the sample will be lysed as hereabove described in step 2 in relation to FIG. 2. A lysis storage 20 is provided to store a lysis buffer before it is pumped in the lysis chamber.

After the lysis step the sample may be pumped to a second process chamber 21 wherein the sample may be enriched in accordance with step 3 and washed and purified in accordance with step 4 as described hereabove. Fluid storages 22 are provided for the storage of different washing and purifying buffers which may be used during the washing and purifying steps. These fluid storages 22 are in fluid communication via valves with the second process chamber 21.

After possible pre-amplification (as described in step 6 in realtion to FIG. 2) which may also be performed in the second process chamber 21 or in the chamber 23, the sample may be introduced in the PCR body 24.

This PCR body 24 is a second application-specific part of the cartridge. The PCR body 24 is circular, disc shaped and connected with a click-fit connection 25 to the generic part 11.

The PCR body 25 comprises six thermocycling chambers 26 so that six PCR processes can be simultaneously be performed on the sample. Such PCR amplification process is hereabove described as step 6 in relation to FIG. 2. Each of the thermocycling chambers 26 is provided with at least one specific primer.

The PCR body 25 may be selected out of a group of different types of PCR bodies each comprising a different set of primers, a different number of chambers and/or a different chamber size or geometry. For instance the PCR body comprising the primers can be selected on the basis of the panels of bacteria/resistances that are to be detected, which selection may be specific for a particular assay or for a particular region, such as Europe, Asia or Africa.

The primers are spotted on a wall of the thermocycling chambers, for instance by an inkjet printing method, so that during storage of the PCR bodies no special measures have to be taken to avoid that the primers flow out of the PCR body, which would for instance be the case if primers in a fluid state would be used. In such case a seal or separate sealed chamber may be provided for holding the primers any other application-specific fluid before use thereof.

After the amplification step the amplified DNA or RNA and preferably the labels that are incorporated in the amplification products are pumped to the detection device 27. This detection device or at least a part thereof is a third application-specific part of the cartridge 10, which is a separate part and can be connected to the generic part 11. In the shown embodiment the detection device is connected to the generic part 11 by a click-fit connection.

Depending on the type of detection method and/or detection means (as described in this application; in particular step six described in relation to FIG. 2), a detection device may be chosen out a series of different application-specific detection devices which may be specially designed for each respective detection method. In some cases the type of detection device that will be used in the cartridge 11 will be dependent on the type of PCR body which is used for the amplification process. Then the choice of a PCR body will automatically lead to a choice of the detection device.

The generic part 11 and the application-specific parts are provided with an identification device, so that after assembly of the generic and application-specific parts it can be checked whether the correct combination is made. Possibly, a more advanced identification system is used, as for instance a RF-tag, which comprises identification tags which automatically can be checked and of which possibly even the history can be tracked. Such checking and history tracking can be controlled by the control unit of the reusable apparatus as a step in the procedure for processing the sample in the cartridge.

An additional advantage of the construction of the present cartridge with a generic part and one or more application-specific parts is that the connection between the generic part and each of the application-specific parts can be easily made airtight, so that the entire space wherein the sample and other fluids used in the cartridge may be closed from the environment In this way contamination of the sample during introduction of the sample in the cartridge and processing thereof is avoided and, since the sample is in a closed environment having its own internal pressure, the processing of the sample can be performed independent of the air pressure in the direct environment, and also independent of other environmental conditions as humidity. This makes a more reliable processing of the sample possible.

It is contemplated that the cartridge according to the present invention may comprise other application-specific parts than the application-specific parts identified in the above description. The application of such other separate application-specific parts in the cartridge are deemed to fall within the scope of the present invention. Examples of such application-specific parts may comprise fluid containers which contain a fluid such as enzymes, reagents, and other chemical substances for a specific application, mixing devices and other mechanical manipulation devices with different geometries or sizes for a specific application and others.

The invention may also be used for specific parts of the cartridge which have to be pre-treated or have to be kept at a certain temperature which is not desired or required for the other parts of the cartridge. For instance, the provision of a separate fluid container which can be used in the pre-treatment or stored at a different location, and which can consequently be connected to the generic part of the cartridge before use, may be very useful since the risk on contamination of that part, in particular the fluid therein is avoided, since the fluid does not have to be transferred from a container to the cartridge in an open environment.

Such use of a separate part is regarded to be application-specific within the meaning of the present invention, even if the same part is used in a number of different applications. An example of such separate part is a separate fluid container for a so-called PCR master mix which has to be stored at a low temperature before use on the cartridge. Just before the cartridge is introduced into the reusable apparatus, the separate fluid container is connected to the generic part of the cartridge, for example by a click fit connection.

The invention claimed is:

1. A cartridge for the detection of the presence, absence and/or amount of a target nucleotide sequence in a sample comprising one or more nucleic acid sequences, comprising:
    a generic part;
    the generic part comprising a click-fit connector, pumps, valves, process chambers, and fluid and waste rooms;
    one or more separate application-specific parts, each being specifically configured for a specific application;
    the one or more application-specific parts being separately connectable to the generic part; and
    at least one of the one or more separate application-specific parts being a PCR body comprising one or more thermocycling chambers and plural primers,
    wherein the one or more thermocycling chambers of the PCR body contains the plural primers for PCR amplification prior to the sample being introduced into the cartridge,
    wherein at least one of the one or more application-specific parts is click-fit connected to the generic part via the click-fit connector,
    wherein at least one of the primers is spotted on the PCR body, and
    wherein the cartridge is configured to be removably connected to an apparatus comprising one or more actuation devices that can actuate one or more elements of the generic part.

2. A cartridge for the detection of the presence, absence and/or amount of a target nucleotide sequence in a sample comprising one or more nucleic acid sequences, comprising:
    a generic part;
    the generic part comprising a releasable click-fit connector, pumps, valves, process chambers, and fluid and waste rooms;
    plural separate application-specific parts, each being specifically configured for a specific application;
    the application-specific parts being separately connectable to the generic part;
    at least one of the separate application-specific parts being a detection device connectable to the generic part, and
    at least one of the separate application-specific parts being a circular, disc-shaped PCR body comprising one or more thermocycling chambers and plural primers,
    wherein the one or more thermocycling chambers of the PCR body contains the plural primers for PCR amplification prior to the sample being introduced into the cartridge,
    wherein at least one of the one or more application-specific parts is click-fit connected to the generic part via the click-fit connector, wherein the PCR body comprises one or more thermal masses, and wherein the cartridge is configured to be removably connected to an apparatus comprising one or more actuation devices that can actuate one or more elements of the generic part.

3. A cartridge for the detection of the presence, absence and/or amount of a target nucleotide sequence in a sample comprising one or more nucleic acid sequences, comprising:
a generic part;
the generic part comprising at least one click-fit connector, pumps, valves, process chambers, and fluid and waste rooms;
one or more separate application-specific parts, each being specifically configured for a specific application;
the one or more application-specific parts being separately connectable to the generic part;
at least one of the one or more separate application-specific parts being a PCR body comprising one or more thermocycling chambers and plural primers; and
a detection device,
wherein the one or more thermocycling chambers of the PCR body contains the plural primers for PCR amplification prior to the sample being introduced into the cartridge and prior to the PCR body being connected to the generic part,
wherein a releasable click-fit connection is provided between the PCR body and the generic part,
wherein the detection device is specifically configured to perform detection with the primers in the PCR body, and
wherein the cartridge is configured to be removably connected to an apparatus comprising one or more actuation devices that can actuate one or more elements of the generic part.

4. A cartridge for the detection of the presence, absence and/or amount of a target nucleotide sequence in a sample comprising one or more nucleic acid sequences, the cartridge comprising:
a generic part;
the generic part comprising a click-fit connector, pumps, valves, process chambers, and fluid and waste rooms;
plural different application-specific parts separate from the generic part;
the plural different application-specific parts being separately connectable to different portions of the generic part; and
at least one of the plural different application-specific parts being a PCR body comprising one or more thermocycling chambers and plural primers,
wherein the one or more thermocycling chambers of the PCR body contains the plural primers for PCR amplification prior to the PCR body being connected to the generic part, and
wherein the cartridge is configured to be removably connected to an apparatus comprising one or more actuation devices that can actuate one or more elements of the generic part.

5. A cartridge according to claim 4, wherein at least one of the primers is spotted on the PCR body.

6. A cartridge according to claim 4, wherein the PCR body is disc-shaped.

7. A cartridge according to claim 4, wherein the PCR body comprises one or more thermal masses.

8. A cartridge according to claim 4, wherein one of the plural different application-specific parts is a detection device.

9. A cartridge according to claim 8, wherein the detection device is selected on the basis of the primers in the PCR body.

10. A cartridge according to claim 4, wherein one of the plural different application-specific parts is a sample introduction device configured to prepare a sample to a specific state.

11. A cartridge according to claim 10, wherein the sample introduction device is a pre-lysis device configured to prepare a sample to a specific state.

12. A cartridge according to claim 4, further comprising spaces for holding a sample or part thereof arranged in each of the generic part and the plural different application-specific parts, wherein each space for holding the sample or part thereof is air-tight.

13. A cartridge according to claim 4, wherein at least one of the plural different application-specific parts comprises an identification device.

14. A cartridge according to claim 4, wherein each of the plural different application-specific parts and the generic part comprises an identification device.

15. A cartridge for detecting a presence, absence and/or amount of a target nucleotide sequence in a sample comprising one or more nucleic acid sequences, the cartridge comprising:
a generic cartridge part comprising a click-fit connector, an identification and a plurality of different devices arranged inside a body of the generic part;
a first application-specific cartridge part comprising an identification and being connectable to the generic part;
a second application-specific cartridge part comprising an identification and being connectable to the generic part;
the first application-specific part being different from the second application-specific part and the first application-specific part comprising a PCR body containing amplification chambers and primers contained in the amplification chambers for PCR amplification; and
the primers being contained within the amplification chambers prior to the first application-specific part being connected to the generic part,
wherein the first part is connected to the generic part via the click-fit connector arranged on the generic part and the second part is connected to the generic part at a location on the generic part that is spaced from the click-fit connector, and
wherein the cartridge, with the first part connected to the generic part via the click-fit connector, is configured to be removably connected to an apparatus comprising one or more actuation devices that can actuate one or more elements of the generic part.

16. The cartridge of claim 15, wherein the cartridge is structured and arranged to receive a sample, perform DNA isolation and amplification, and detect amplified DNA, wherein the plurality of different devices comprises at least one of:
pumps;
valves;
process chambers; and
fluid and waste rooms.

* * * * *